(12) United States Patent
Liu et al.

(10) Patent No.: US 11,308,603 B2
(45) Date of Patent: Apr. 19, 2022

(54) DETECTION AND MONITORING OF WASTE DISPOSAL IN AN ENVIRONMENTAL LOCATION USING ARTIFICIAL INTELLIGENCE

(71) Applicant: International Business Machines Corporation, Armonk, NY (US)

(72) Inventors: Na Liu, Xi'an (CN); Mei Rui Su, Beijing (CN); Pei Jian Liu, Beijing (CN); Bing Hua Zhao, Beijing (CN); Yan Liu, Beijing (CN); Zhong Fang Yuan, Xi'an (CN); Wen Wang, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 45 days.

(21) Appl. No.: 16/991,022

(22) Filed: Aug. 12, 2020

(65) Prior Publication Data

US 2022/0051388 A1    Feb. 17, 2022

(51) Int. Cl.
*G06T 7/00* (2017.01)
*G01N 33/18* (2006.01)
*G06T 7/246* (2017.01)

(52) U.S. Cl.
CPC ........... *G06T 7/0004* (2013.01); *G01N 33/18* (2013.01); *G06T 7/246* (2017.01);
(Continued)

(58) Field of Classification Search
CPC ................... G06T 7/0004; G06T 7/246; G06T 2207/10032; G06T 2207/20081; G06T 2207/20084; G01N 33/18
See application file for complete search history.

(56) References Cited

U.S. PATENT DOCUMENTS

| 8,801,930 B2 * | 8/2014 | Qiu | B09B 3/00 |
| | | | 210/603 |
| 10,713,599 B2 * | 7/2020 | Podgorny | B65F 3/00 |

(Continued)

FOREIGN PATENT DOCUMENTS

| CN | 106741894 A | 5/2017 |
| CN | 108646728 A | 10/2018 |

(Continued)

OTHER PUBLICATIONS

Aishwarya, et al., "Detection and Removal of Floating Wastes on Water Bodies", International Journal of Research and Scientific Innovation (IJRSI), vol. IV, Issue VI, Jun. 2017, pp. 19-22, <https://www.rsisinternational.org/IJRSI/Issue41/19-22.pdf>.

(Continued)

*Primary Examiner* — Bobbak Safaipour
(74) *Attorney, Agent, or Firm* — Michael A. Petrocelli

(57) ABSTRACT

Monitoring of an environmental location to detect waste disposal includes receiving, by a computer, a collection of images from aerial data acquisition sources, the collection of images corresponding to the environmental location and the waste disposed in the environmental location. The collection of images are processed by the computer to extract properties of the waste and first properties of the environmental location. Subsequently, the properties of the waste disposed in the environmental location are classified according to a class. Additional information from external data sources including second properties of the environmental location is received by the computer. The computer determines a behavior of waste disposal in the environmental location over a period of time based on the classified properties of the disposed waste and the first and second properties of the environmental location, and generated a remediation plan based on the determined behavior.

17 Claims, 6 Drawing Sheets

(52) U.S. Cl.
    CPC ............... *G06T 2207/10032* (2013.01); *G06T 2207/20081* (2013.01); *G06T 2207/20084* (2013.01)

(56) References Cited

U.S. PATENT DOCUMENTS

| | | | |
|---|---|---|---|
| 11,172,171 B1* | 11/2021 | Skolnick | ................ H04N 7/188 |
| 2017/0364872 A1* | 12/2017 | Rodoni | ............ G06Q 10/06315 |
| 2020/0208368 A1* | 7/2020 | Milanovich | ............. E02B 15/10 |
| 2021/0217156 A1* | 7/2021 | Balachandran | .... G01G 23/3735 |
| 2021/0357830 A1* | 11/2021 | Kyochika | .............. G06Q 50/26 |

FOREIGN PATENT DOCUMENTS

| | | |
|---|---|---|
| CN | 107622231 B | 11/2019 |
| IN | 201821029064 A | 7/2020 |

OTHER PUBLICATIONS

Mell et al., "The NIST Definition of Cloud Computing", National Institute of Standards and Technology, Special Publication 800-145, Sep. 2011, 7 pages.

\* cited by examiner

DETECTION AND MONITORING OF WASTE DISPOSAL IN AN ENVIRONMENTAL LOCATION USING ARTIFICIAL INTELLIGENCE

BACKGROUND

The present invention generally relates to the field of environmental cleanup and management, and more particularly to cleanup and management of polluted water bodies by monitoring and detecting waste disposal using machine learning techniques.

One area of environment maintenance and pollution is directed to water pollution. Water pollution is the contamination of water bodies, usually as a result of human activities. Water bodies include, for example, lakes, rivers, oceans, aquifers, and groundwater. Uncontrolled disposal of anthropogenic waste (e.g., municipal solid waste, agricultural and animal waste, medical waste, radioactive waste, hazardous waste, industrial non-hazardous waste, construction and demolition debris, extraction and mining waste, oil and gas production waste, etc.) on water bodies is the main cause of water pollution. Water pollution can result in human health problems, poisoned wildlife, and long-term ecosystem damage.

SUMMARY

Shortcomings of the prior art are overcome and additional advantages are provided through the provision of a computer-implemented method for monitoring and detecting waste disposal in an environmental location that includes receiving, by a computer, a collection of images from aerial data acquisition sources, the collection of images corresponding to the environmental location and the waste disposed in the environmental location. The collection of images are processed to extract data including properties of the waste and first properties of the environmental location. Extracted properties of the waste disposed in the environmental location are classified according to a class. Additional information including second properties of the environmental location can be obtained from external data sources and used together with the classified properties of the waste and the first properties of the environmental location to determine a behavior of waste disposal in the environmental location over a period of time. Finally, a remediation plan is generated according to the determined behavior of waste disposal in the environmental location.

Another embodiment of the present disclosure provides a computer program product for monitoring and detecting waste disposal in an environmental location, based on the method described above.

Another embodiment of the present disclosure provides a computer system for monitoring and detecting waste disposal in an environmental location, based on the method described above.

BRIEF DESCRIPTION OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
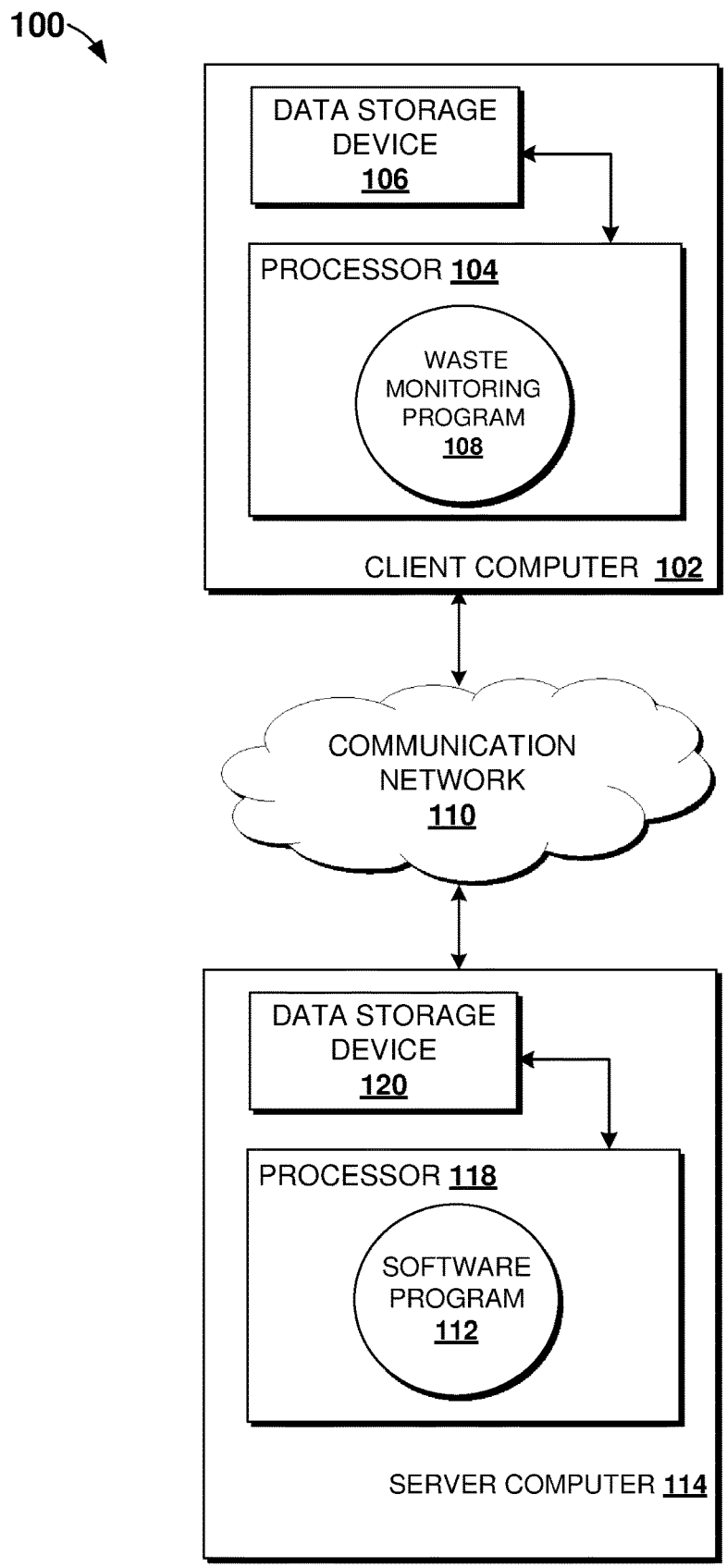
FIG. 1 is a block diagram illustrating a networked computer environment, according to an embodiment of the present disclosure.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Disposal of anthropogenic waste in environmental sites such as rivers, streams, and oceans is the main cause of water pollution. Approximately 80% of marine litter comes from land sources. Rainwater and wind carries waste into streams and rivers that inflow into the ocean. This makes detection and monitoring of waste disposal in offshore as well as onshore environmental locations critical to prevent water and land pollution. Particularly important is the monitoring and detection of waste accumulation in naturally flowing watercourse (i.e., rivers) that flow towards oceans, seas, lakes, or another rivers.

The large areas typically occupied by water bodies may hinder activities related to the monitoring, detection, and collection of waste. Additionally, since current remediation methods rely mainly on manpower, when waste is located in areas difficult to reach, remediation activities can be difficult and pose safety risks to cleaning personnel.

Therefore, embodiments of the present invention provide a method, system, and computer program product for monitoring and detecting waste disposal in various environmental locations using artificial intelligence (AI). The following described exemplary embodiments provide a system, method, and computer program product to, among other things, collect data including location, volume, and type of waste disposed in environmental sites including water bodies and land surfaces, and generate, based on the collected data, a remediation plan according to which cleanup activities can be coordinated by government or private entities.

Additionally, embodiments of the present disclosure can track changes on waste accumulation, and forecast a frequency and quantity of waste accumulation behavior based on historical data. This forecast can be used by environmental agencies to prepare contingency plans and coordinate cleanup activities. The present embodiments can also use external sources to determine, for example, a flow direction of a water body that can help predicting a path for the disposed waste and planning downstream cleanup activities. Thus, the present embodiments have the capacity to improve the technical field of environmental cleanup and management by providing information regarding the location, size, and type of waste disposed at or near an environmental location, the information further includes specific geographic coordinates, a volume, a frequency of accumulation, geographical features, and a direction of flow of water bodies that can be used to coordinate remediation activities in a safe and efficient manner.

Referring now to FIG. 1, an exemplary networked computer environment 100 is depicted, according to an embodiment of the present disclosure. FIG. 1 provides only an illustration of one embodiment and does not imply any limitations with regard to the environments in which different embodiments may be implemented. Many modifications to the depicted environment may be made by those skilled in the art without departing from the scope of the invention, as recited by the claims.

The networked computer environment 100 may include a client computer 102 and a communication network 110. The client computer 102 may include a processor 104, that is enabled to run a waste monitoring program 108, and a data storage device 106. Client computer 102 may be, for example, a mobile device, a telephone (including smartphones), a personal digital assistant, a netbook, a laptop computer, a tablet computer, a desktop computer, or any type of computing devices capable of accessing a network.

The networked computer environment 100 may also include a server computer 114 with a processor 118, that is enabled to run a software program 112, and a data storage device 120. In some embodiments, server computer 114 may be a resource management server, a web server or any other electronic device capable of receiving and sending data. In another embodiment, server computer 114 may represent a server computing system utilizing multiple computers as a server system, such as in a cloud computing environment.

The waste monitoring program 108 running on client computer 102 may communicate with the software program 112 running on server computer 114 via the communication network 110. As will be discussed with reference to FIG. 4, client computer 102 and server computer 114 may include internal components and external components.

The networked computer environment 100 may include a plurality of client computers 102 and server computers 114, only one of which is shown. The communication network 110 may include various types of communication networks, such as a local area network (LAN), a wide area network (WAN), such as the Internet, the public switched telephone network (PSTN), a cellular or mobile data network (e.g., wireless Internet provided by a third or fourth generation of mobile phone mobile communication), a private branch exchange (PBX), any combination thereof, or any combination of connections and protocols that will support communications between client computer 102 and server computer 114, in accordance with embodiments of the present disclosure. The communication network 110 may include wired, wireless or fiber optic connections. As known by those skilled in the art, the networked computer environment 100 may include additional computing devices, servers or other devices not shown.

Plural instances may be provided for components, operations, or structures described herein as a single instance. Boundaries between various components, operations, and data stores are somewhat arbitrary, and particular operations are illustrated in the context of specific illustrative configurations. Other allocations of functionality are envisioned and may fall within the scope of the present invention. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the present invention.

Figure 2:
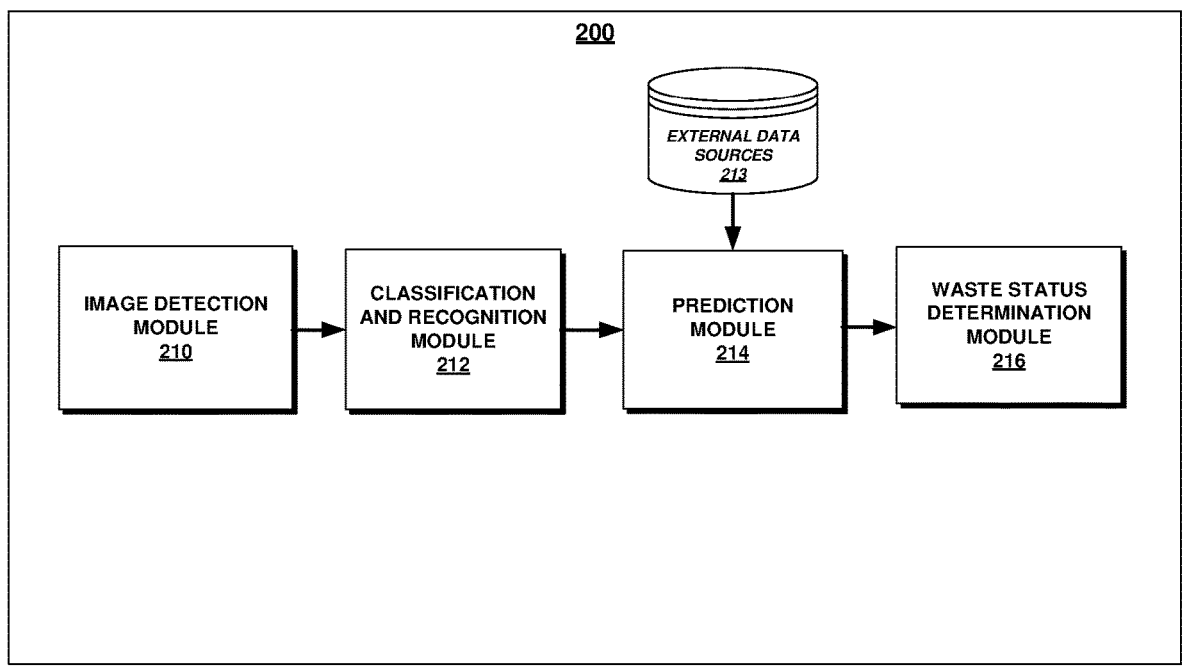
FIG. 2 depicts a system for monitoring and detecting waste disposal in an environmental location using machine learning techniques, according to an embodiment of the present disclosure.

Referring now to FIG. 2, a system 200 for monitoring and detecting waste disposal in an environmental location using machine learning techniques is shown, according to an embodiment of the present disclosure. The system 200 can be implemented in, for example, the client computer 102 of FIG. 1.

According to an embodiment, the system 200 includes an image detection module 210, a classification and recognition module 212, a prediction module 214, and a waste status determination module 216. The image detection module 210 collects images corresponding to an environmental location from available data acquisition sources. The environmental location may include landforms and/or water bodies at risk of being polluted, or any polluted site that requires maintenance and active monitoring. For illustration purposes only, without intent of limitations, embodiments of the present disclosure will be explained using a water body (e.g., river, stream, ocean, etc.) as primary example. However, it may be understood that embodiments of the present disclosure can be implemented in different environmental sites where waste disposal can occur. For instance, exemplary environmental locations where waste disposal and accumulation can occur may include offshore locations (e.g., rivers, oceans, lakes, etc.) and onshore locations (e.g., mountains, natural landmarks, etc.).

In a preferred embodiment, different data acquisition sources include unmanned aerial vehicles (UAV), satellite-based systems, and the like. The collected images are processed to obtain geographic coordinates of the environmental location and waste that may be disposed in or near the environmental location For example, a longitude, a latitude, and an altitude of a water body and disposed waste can be identified from the collected images. In addition to geographic coordinates, temporal information (e.g., from image timestamp), a class and a size of the disposed waste can be obtained from the collected images. In one embodiment, types of waste that can be identified by the image detection module 210 may include, but is not limited to, floating waste (e.g., plastic, municipal solid waste, oil from oil spills, etc.), waste located in areas surrounding the water body (e.g., shoreside), and organic waste (e.g., dead fish, green algae, etc.). Known image processing techniques can be used to extract information from the collected images.

The classification and recognition module 212 receives information from the image detection module 210, and classifies it using a classification model based on a convolutional neural network (CNN) approach (hereinafter referred to as "CNN classification model"). As known by those skilled in the art, CNN is a class of deep learning neural networks for image recognition and classification capable of analyzing an input (i.e., image) and outputting a class or a probability that the input is a particular class.

Specifically, data from the image detection module 210 is used by the classification and recognition module 212 to train the CNN classification model to recognize a type of waste disposed in the environmental location (e.g., the water body). Through the CNN classification model, different types of waste can be arrange according to a class or type. Further, the CNN classification model can identify a size of the waste based on information collected from the data acquisition sources (e.g., a size of the waste can be determined based on a height of the UAV monitoring the area). According to an embodiment, the classification and recognition module 212 can identify waste floating on the monitored water body as well as waste located in areas surrounding the water body (e.g., shoreside). Output data from the classification and recognition module 212 will be used as input data for the prediction module 214.

The prediction module 214 receives output data from the classification and recognition module 212. Additionally, the prediction module 214 receives additional information from external data sources. The external data sources may include, but are not limited to, government or environmental agencies databases, weather forecast websites, etc. In an exemplary embodiment, the information collected from external data sources may include, but is not limited to, properties or characteristics of the water body (e.g., a flow direction, a depth, a speed, etc.), and atmospheric conditions (e.g., temperature, wind and precipitation conditions, etc.). In embodiments in which the environmental location includes landforms, the information collected from external data sources may include characteristics such as elevation, slope, orientation, stratification, rock exposure, soil type, vegetation, and various topographic elements including manmade features such as roads, damns, etc.

The information received by the prediction module 214 is used to train and calibrate a prediction model based on a Recurrent Neural Network (RNN) approach (hereinafter referred to as "RNN prediction model"). As known by those skilled in the art, RNN is a type of artificial neural network commonly used in speech recognition and natural language processing (NLP) technologies. RNNs are designed to recognize data's sequential characteristics and use patterns to predict the next likely scenario. Specifically, the RNN prediction model can predict or forecast a time and frequency of waste accumulation in the area under study in combination with atmospheric conditions.

Results from the RNN prediction model are used by the waste status determination module 216 to determine current and future attributes of the waste and of the environmental location (e.g., water body) in which it has been disposed. Specifically, the waste status determination module 216 can, based on the RNN prediction model and related historical data, determine specific characteristics and behavior of both environmental location and disposed waste that can be used to generate a remediation plan. For example, the waste status determination module 216 can, using results from the RNN prediction model, generate the following information regarding the disposed waste "floating solid waste located on the Weihe River in China occupying an area of two (2) square meters, with coordinates of 108 degrees 37 minutes east longitude in Hu County, Xi'an, 34 degrees 7 minutes north latitude".

Further, the RNN prediction model can forecast future waste accumulation in the environmental location and surrounding areas during a certain period of time. Output information from the waste status determination module 216 can be used by public and private agencies to define an efficient clean up strategy. For example, a size and number of clean up equipment (e.g., trucks, vessels, tools), and remediation personnel can be determined based on the output information from the waste status determination module 216 (e.g., size and type of the waste). In some embodiments, the waste status determination module 216 may track changes in waste accumulation at or near the environmental location during a period of time, and use this information to forecast an accumulation frequency based on which a remediation schedule can be created including areas of higher priority for environmental remediation.

In some embodiments, in response to the frequency and amount of waste accumulation, the setup of a waste disposal units can be recommended for the monitored environmental location.

Figure 3:
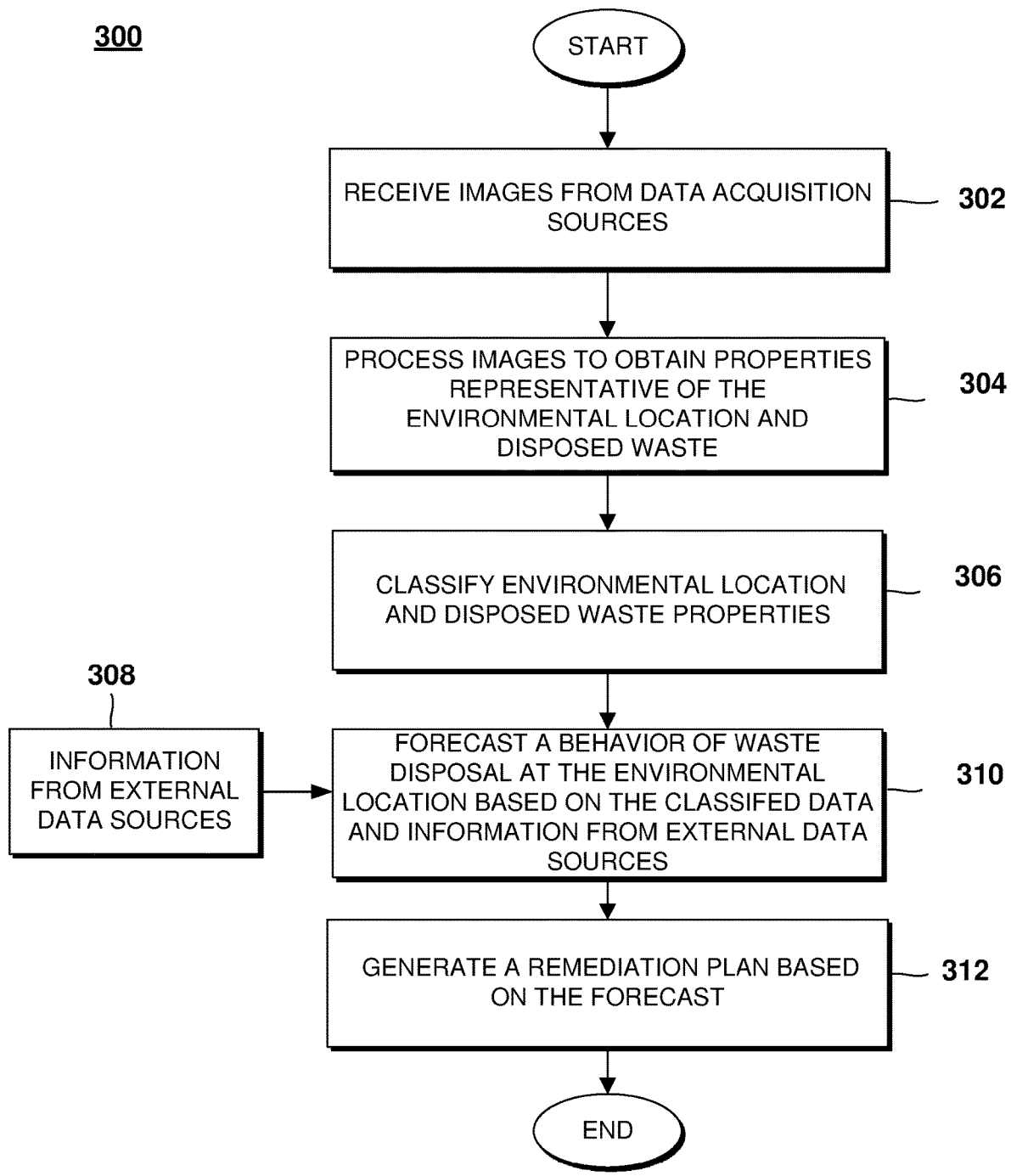
FIG. 3 depicts a flowchart illustrating the steps of a computer-implemented method for monitoring and detecting waste disposal in an environmental location using machine learning techniques, according to an embodiment of the present disclosure.

Referring now to FIG. 3, a flowchart illustrating the steps of a computer-implemented method for monitoring and detecting waste disposal in an environmental location using machine learning techniques is shown, according to an embodiment of the present disclosure.

The method starts at step 302 by receiving images from one or more data acquisition sources. The data acquisition sources include different aerial data acquisition devices such as unmanned aerial vehicles or satellites. The aerial data acquisition devices collect images corresponding to the environmental location, disposed waste, and surrounding areas. In this embodiment, the environmental location includes a body of water such as, for example, waterways, rivers, pond, lake, oceans, etc. However, as explained above, the environmental location can also include places situated or occurring on land. The received images are processed at step 304 to extract a plurality of parameters associated with attributes of the environmental location and disposed waste, including, for example, geographic coordinates of both disposed waste and environmental location, and temporal information. Any known image processing technique can be used to extract information from the received images.

The information extracted at step 304 is used to train the CNN classification model, described above with reference to FIG. 2, to recognize different types of waste (e.g., anthropogenic solid and/or liquid waste, organic waste, floating or shoreside waste, etc.) and classify, at step 306, the detected waste according to a class or type based on the trained model. Stated differently, data from step 304 is fed to the CNN classification model, to categorize relevant features of the disposed waste.

In addition to the information classified at step 306, additional information regarding the environmental location (e.g., water body) and atmospheric conditions can be obtained from external data sources at step 308. The additional information may include, but is not limited to, flow direction of the water body, water depth, flow velocity, temperature, wind speed, etc. The external data sources may include public (e.g., government) or private (e.g., companies) databases, weather forecast websites, and the like.

The collected information from steps 306, 308 can then be used to forecast a behavior of waste disposal over a period of time on the environmental location under study. Specifically, the classified data (step 306) and data from external data sources (308) can be used as input for training an RNN prediction model described above with reference to FIG. 2. By doing this, specific characteristics of both environmental location and disposed waste can be obtained and used to determine current and future behavior of waste disposal in the environmental location under study. It should be noted that the environmental location under study (i.e., area of study or monitored area) includes the environmental location and areas surrounding the environmental location.

Finally, results from the RNN prediction model can be used to generate a remediation plan that can be shared with environmental authorities and government agencies for its implementation.

Therefore, embodiments of the present disclosure provide a method, system and computer program product to, among other things, efficiently determine properties corresponding to waste disposed in an environmental location from aerial data acquisition devices and external data sources to predict the behavior of waste accumulation over a period of time in monitored environmental locations (water bodies or land surfaces), and generate an action plan to remove the disposed waste, including equipment required to perform remediation activities, that can be shared with environmental agencies for its execution.

Figure 4:
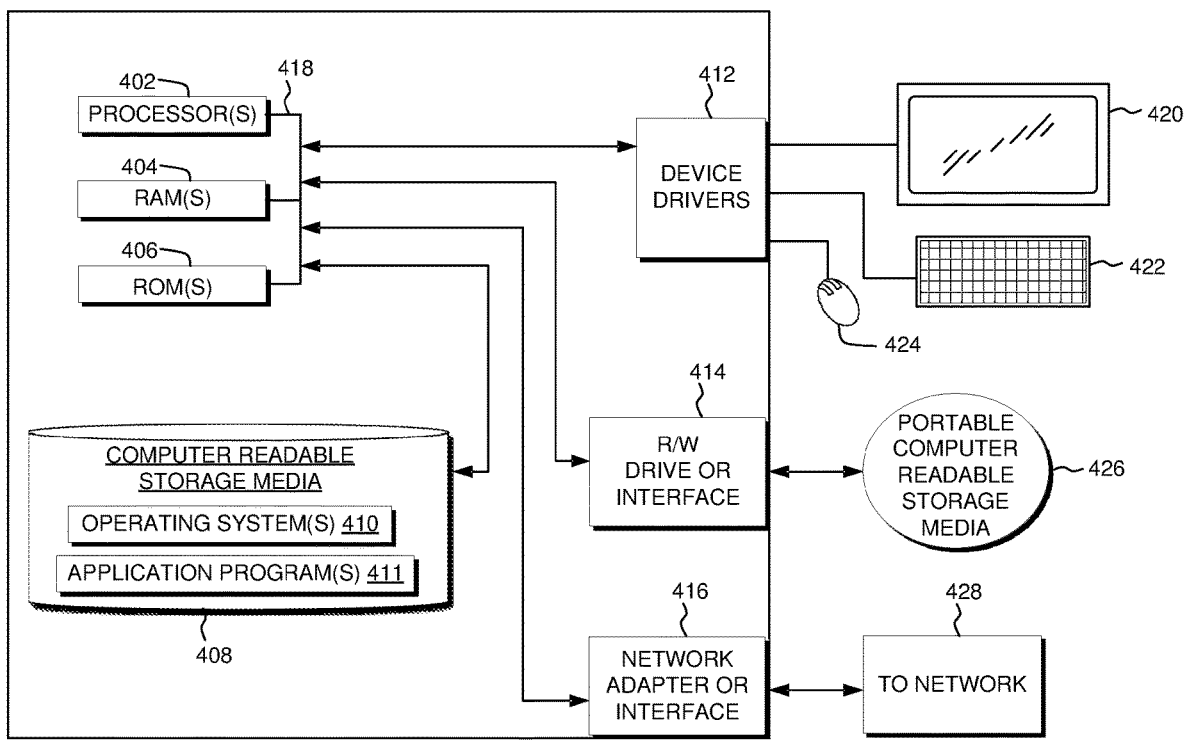
FIG. 4 is a block diagram of internal and external components of a computer system, according to an embodiment of the present disclosure.

Referring now to FIG. 4, a block diagram of components of client computer 102 and server computer 114 of networked computer environment 100 of FIG. 1 is shown, according to an embodiment of the present disclosure. It should be appreciated that FIG. 4 provides only an illustration of one implementation and does not imply any limitations regarding the environments in which different embodiments may be implemented. Many modifications to the depicted environment may be made.

Client computer 102 and server computer 114 may include one or more processors 402, one or more computer-readable RAMs 404, one or more computer-readable ROMs 406, one or more computer readable storage media 408, device drivers 412, read/write drive or interface 414, network adapter or interface 416, all interconnected over a communications fabric 418. Communications fabric 418 may be implemented with any architecture designed for passing data and/or control information between processors (such as microprocessors, communications and network processors, etc.), system memory, peripheral devices, and any other hardware components within a system.

One or more operating systems 410, and one or more application programs 411 are stored on one or more of the computer readable storage media 408 for execution by one or more of the processors 402 via one or more of the respective RAMs 404 (which typically include cache memory). In the illustrated embodiment, each of the computer readable storage media 408 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Client computer 102 and server computer 114 may also include a R/W drive or interface 414 to read from and write to one or more portable computer readable storage media 426. Application programs 411 on client computer 102 and server computer 114 may be stored on one or more of the portable computer readable storage media 426, read via the respective R/W drive or interface 414 and loaded into the respective computer readable storage media 408.

Client computer 102 and server computer 114 may also include a network adapter or interface 416, such as a TCP/IP adapter card or wireless communication adapter (such as a 4G wireless communication adapter using OFDMA technology) for connection to a network 428. Application programs 411 on client computer 102 and server computer 114 may be downloaded to the computing device from an external computer or external storage device via a network (for example, the Internet, a local area network or other wide area network or wireless network) and network adapter or interface 416. From the network adapter or interface 416, the programs may be loaded onto computer readable storage media 408. The network may comprise copper wires, optical fibers, wireless transmission, routers, firewalls, switches, gateway computers and/or edge servers.

Client computer 102 and server computer 114 may also include a display screen 420, a keyboard or keypad 422, and a computer mouse or touchpad 424. Device drivers 412 interface to display screen 420 for imaging, to keyboard or keypad 422, to computer mouse or touchpad 424, and/or to display screen 420 for pressure sensing of alphanumeric character entry and user selections. The device drivers 412, R/W drive or interface 414 and network adapter or interface 416 may include hardware and software (stored on computer readable storage media 408 and/or ROM 406).

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
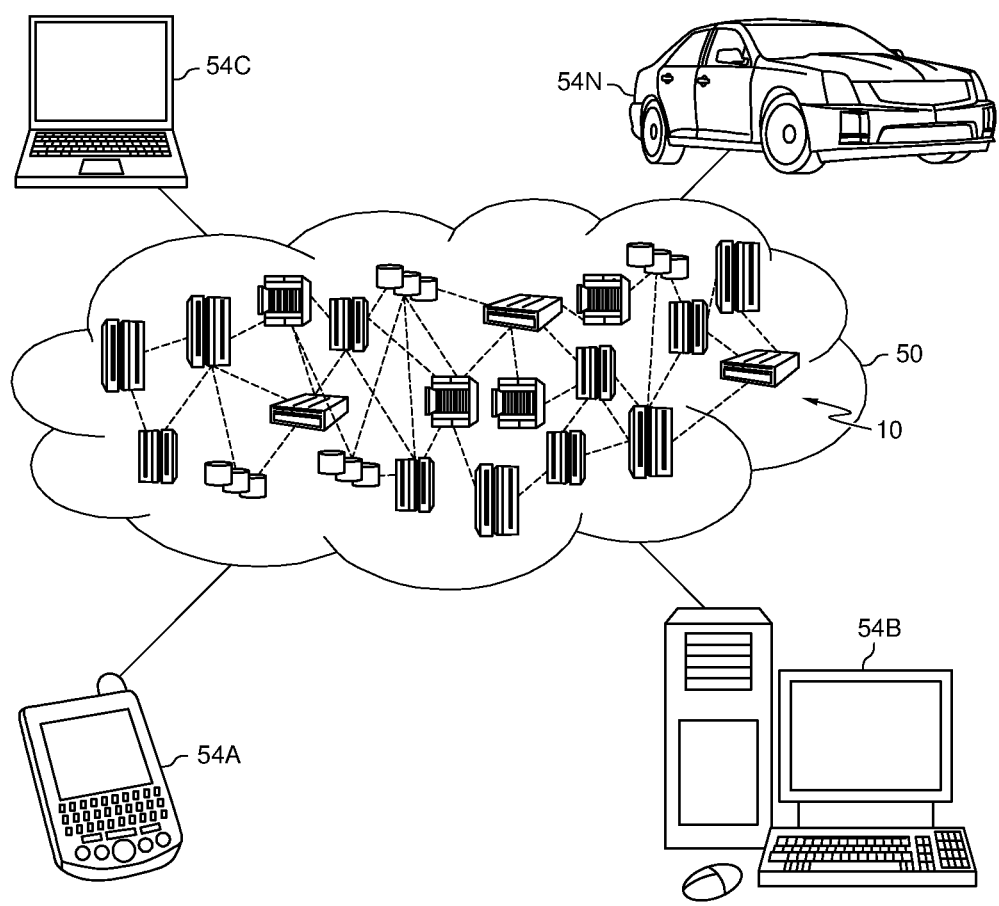
FIG. 5 is a block diagram of an illustrative cloud computing environment, according to an embodiment of the present disclosure.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
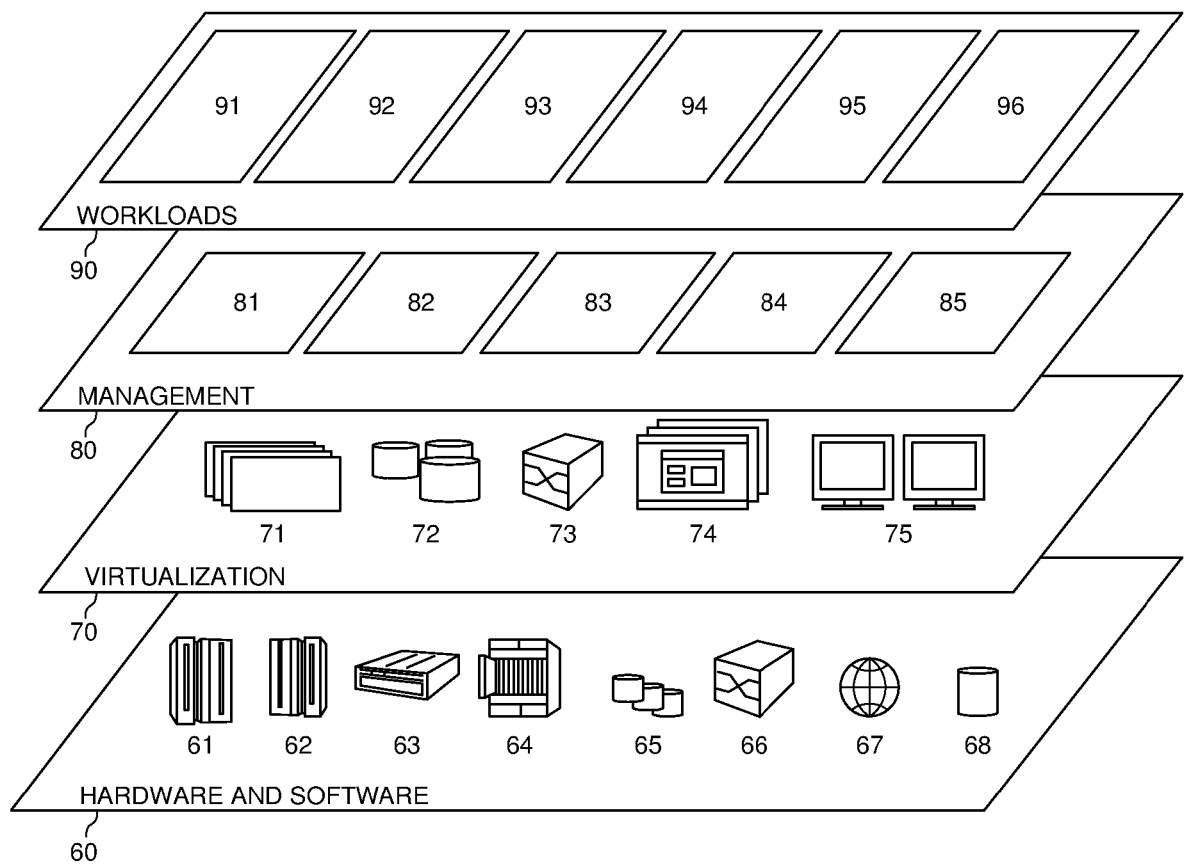
FIG. 6 is a block diagram of functional layers of the illustrative cloud computing environment of FIG. 5, according to an embodiment of the present disclosure.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and system for waste monitoring and management in environmental locations 96.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While steps of the disclosed method and components of the disclosed systems and environments have been sequentially or serially identified using numbers and letters, such numbering or lettering is not an indication that such steps must be performed in the order recited, and is merely provided to facilitate clear referencing of the method's steps. Furthermore, steps of the method may be performed in parallel to perform their described functionality.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for monitoring and detecting waste disposal in an environmental location, comprising:
    receiving, by a computer, a collection of images from aerial data acquisition sources, the collection of images corresponding to the environmental location and a waste disposed in the environmental location, wherein the environmental location includes a water body;
    processing, by the computer, the collection of images to extract data comprising properties of the waste and first properties of the environmental location, the first properties of the environmental location including geographic coordinates and a temporal information associated with the environmental location;
    classifying, by the computer, the properties of the waste disposed in the environmental location according to a class;
    receiving, by the computer, additional information from external data sources, the additional information comprising second properties of the environmental location, the second properties of the environmental location including a water flow direction, a velocity, and a depth associated with the environmental location;
    determining, by the computer, a behavior of waste disposal in the environmental location over a period of time based on the classified properties of the waste disposed in the environmental location and the first and second properties of the environmental location; and
    generating, by the computer, a remediation plan according to the determined behavior of waste disposal in the environmental location.

2. The method of claim 1, further comprising:
    predicting, by the computer, a waste accumulation frequency in the environmental location over the period of time.

3. The method of claim 1, wherein the aerial data acquisition sources comprise unmanned aerial vehicles and satellite-based systems.

4. The method of claim 1, wherein the properties of the waste comprise geographic coordinates, a type and a size of the waste disposed in the environmental location.

5. The method of claim 1, wherein classifying the properties of the waste disposed in the environmental location is performed using a Convolutional Neural Network model.

6. The method of claim 1, wherein determining the behavior of waste disposal in the environmental location over the period of time is performed using a Recurrent Neural Network model.

7. A computer system for monitoring and detecting waste disposal in an environmental location, comprising:
    one or more processors, one or more computer-readable memories, one or more computer-readable tangible storage devices, and program instructions stored on at least one of the one or more storage devices for execution by at least one of the one or more processors via at least one of the one or more memories, wherein the computer system is capable of performing a method comprising:
    receiving, by a computer, a collection of images from aerial data acquisition sources, the collection of images corresponding to the environmental location and a waste disposed in the environmental location, wherein the environmental location includes a water body;
    processing, by the computer, the collection of images to extract data comprising properties of the waste and first properties of the environmental location, the first properties of the environmental location including geographic coordinates and a temporal information associated with the environmental location;
    classifying, by the computer, the properties of the waste disposed in the environmental location according to a class;
    receiving, by the computer, additional information from external data sources, the additional information comprising second properties of the environmental location, the second properties of the environmental location including a water flow direction, a velocity, and a depth associated with the environmental location;
    determining, by the computer, a behavior of waste disposal in the environmental location over a period of time based on the classified properties of the waste disposed in the environmental location and the first and second properties of the environmental location; and
    generating, by the computer, a remediation plan according to the determined behavior of waste disposal in the environmental location.

8. The computer system of claim 7, further comprising:
    predicting, by the computer, a waste accumulation frequency in the environmental location over the period of time.

9. The computer system of claim 7, wherein the aerial data acquisition sources comprise unmanned aerial vehicles and satellite-based systems.

10. The computer system of claim 7, wherein the properties of the waste comprise geographic coordinates, a type and a size of the waste.

11. The computer system of claim 7, wherein classifying the properties of the waste disposed in the environmental location is performed using a Convolutional Neural Network model.

12. The computer system of claim 7, wherein determining the behavior of waste disposal in the environmental location over the period of time is performed using a Recurrent Neural Network model.

13. A computer program product for monitoring and detecting waste disposal in an environmental location, comprising:
one or more computer readable storage media, and program instructions collectively stored on the one or more computer readable storage media, the program instructions comprising:
program instructions to receive, by a computer, a collection of images from aerial data acquisition sources, the collection of images corresponding to the environmental location and a waste disposed in the environmental location, wherein the environmental location includes a water body;
program instructions to process, by the computer, the collection of images to extract data comprising properties of the waste and first properties of the environmental location, the first properties of the environmental location including geographic coordinates and a temporal information associated with the environmental location;
program instructions to classify, by the computer, the properties of the waste disposed in the environmental location according to a class;
program instructions to receive, by the computer, additional information from external data sources, the additional information comprising second properties of the environmental location, the second properties of the environmental location including a water flow direction, a velocity, and a depth associated with the environmental location;
program instructions to determine, by the computer, a behavior of waste disposal in the environmental location over a period of time based on the classified properties of the waste disposed in the environmental location and the first and second properties of the environmental location; and
program instructions to generate, by the computer, a remediation plan according to the determined behavior of waste disposal in the environmental location.

14. The computer program product of claim 13, further comprising:
program instructions to predict, by the computer, a waste accumulation frequency in the environmental location over the period of time.

15. The computer program product of claim 13, wherein the aerial data acquisition sources comprise unmanned aerial vehicles and satellite-based systems.

16. The computer program product of claim 13, wherein the properties of the waste comprise geographic coordinates, a type and a size of the waste.

17. The computer program product of claim 13, wherein the program instructions to classify the properties of the waste disposed in the environmental location comprise program instructions to use a Convolutional Neural Network model, and wherein the program instructions to determine the behavior of waste disposal in the environmental location over the period of time comprise program instructions to use a Recurrent Neural Network model.

* * * * *